United States Patent [19]

Bauer et al.

[11] Patent Number: 4,512,782

[45] Date of Patent: Apr. 23, 1985

[54] MULTISTAGE RECTIFICATION OF GASEOUS HYDROCARBONS CONTAINING SOUR GASES

[75] Inventors: Heinz Bauer, Neuried; Hans Becker, Munich, both of Fed. Rep. of Germany

[73] Assignee: Linde Aktiengesellschaft, Wiesbaden, Fed. Rep. of Germany

[21] Appl. No.: 576,506

[22] Filed: Feb. 2, 1984

[30] Foreign Application Priority Data

Feb. 3, 1983 [DE] Fed. Rep. of Germany ....... 3303651

[51] Int. Cl.³ .............................................. B01D 19/00
[52] U.S. Cl. .......................................... 55/48; 55/68; 55/73; 202/154; 203/78
[58] Field of Search ......................... 55/48, 51, 68, 73; 62/24, 27; 202/154; 203/78

[56] References Cited

U.S. PATENT DOCUMENTS

| | | | |
|---|---|---|---|
| 2,451,136 | 10/1948 | Wenzke | 55/51 |
| 2,661,812 | 12/1953 | Gilmore | 55/51 |
| 2,742,103 | 4/1956 | Adams | 55/48 |
| 2,930,752 | 3/1960 | Swerdloff | 55/51 |
| 3,102,012 | 8/1963 | Dowd | 55/48 |
| 3,134,726 | 5/1964 | Hochgraf | 55/48 |

*Primary Examiner*—Charles Hart
*Attorney, Agent, or Firm*—Millen & White

[57] ABSTRACT

In the fractionation of a gaseous mixture under pressure containing methane, ethane, propane, inert gases, higher hydrocarbons, hydrogen sulfide, as well as carbon dioxide, e.g., a natural gas, the higher hydrocarbons are obtained by rectification as bottoms product, whereas methane, ethane, propane, hydrogen sulfide and carbon dioxide comprise the head product. The rectification is conducted in three stages, wherein the separated head product of the second stage forms at least in part the reflux of the first stage. By means of this process, a $C_{4+}$ hydrocarbon condensate free of sour gases, as well as a $C_{3-}$ head fraction of high purity are obtained.

19 Claims, 1 Drawing Figure

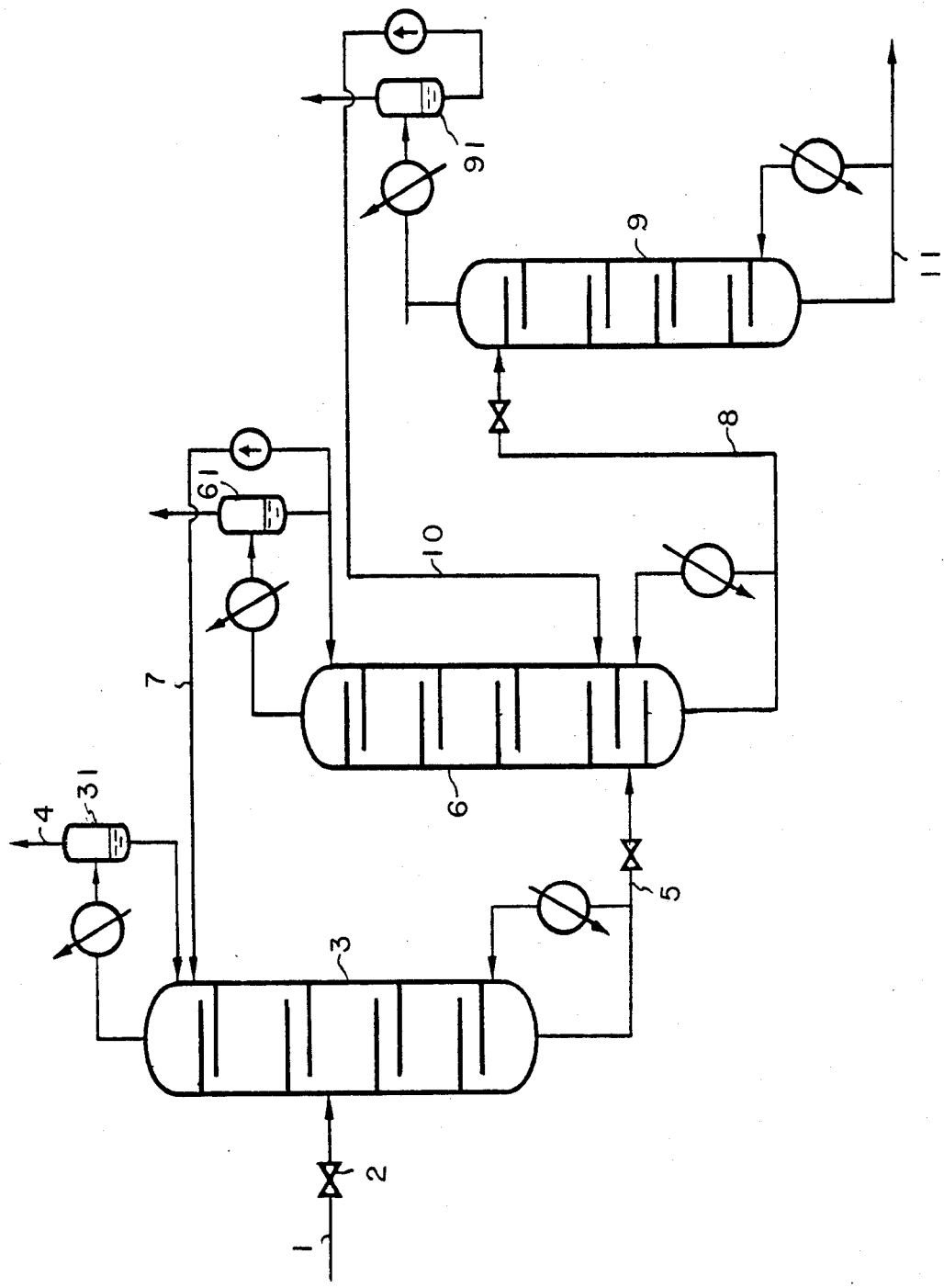

MULTISTAGE RECTIFICATION OF GASEOUS HYDROCARBONS CONTAINING SOUR GASES

BACKGROUND OF THE INVENTION

This invention relates to a process for the fractionation of a gaseous mixture under pressure, this mixture containing generally methane, ethane, propane, inert gases such as nitrogen, higher hydrocarbons ($C_{4+}$), hydrogen sulfide and carbon dioxide.

In heavy natural gases having a high content of sour gas, the $C_{4+}$ hydrocarbons must generally be separated before removing the sour gas from the natural gas by physical scrubbing steps since, on the one hand, further processing of the sour gases in a Claus plant is subject to a low tolerance of $C_{4+}$ components, and, on the other hand, it is desirable to obtain a high yield of $C_{4+}$ which can be utilized either as fuel or as a starting material for chemical syntheses. The pre-separation of the $C_{4+}$ fraction is generally accomplished by fractional condensation and/or rectification.

DOS No. 2,828,498 discloses a process for natural gas fractionation by rectification and methanol scrubbing. This process is conducted in such a way that, in the rectification step, not only a large portion of the higher hydrocarbons, but also hydrogen sulfide and, in certain cases, a portion of the carbon dioxide are obtained as rectification bottoms. The methanol scrubbing step is employed to remove carbon dioxide and, in some cases, small amounts of hydrogen sulfide and heavy hydrocarbons from the rectification head product. This process however, is unsuitable for the processing of natural gases having a very high content of sour gases, e.g., having at least 1 mole percent, especially at least 5 mole percent of sour gases.

SUMMARY

An object of the present invention is to provide an improved process and associated apparatus to achieve a high $C_{3-}$ purity and a large $C_{4+}$ yield from gaseous mixtures also containing methane, ethane and sour gases, especially from gaseous mixtures having a high content of sour gases. also exhibits reduced energy demands as compared to prior processes.

Upon further study of the specification and appended claims, further objects and advantages of this invention will become apparent to those skilled in the art.

These objects are attained according to this invention by conducting the rectification in three stages; separating, in the first stage, a head product almost free of $C_{4+}$ hydrocarbons; passing bottoms from the first stage to the second stage and separating therein further $C_{3-}$ hydrocarbons as well as a portion of the hydrogen sulfide as the head product and recycling the second stage head product into the first stage at least in part as reflux for the first stage; passing bottoms from said second stage to the third stage, and separating therein residual hydrogen sulfide as well as residual portions of $C_{3-}$ hydrocarbons as the head product and either recycling the third stage head product into the second stage or withdrawing same as a separate partial stream; and withdrawing from the bottom of the third stage $H_2S$-free $C_{4+}$ hydrocarbons. The importance of the provision that the separated head product of the second stage constitutes at least in part the reflux of the first stage is explained below.

An aspect of this invention is the desirability of operating in the proximity of the ambient temperature under a pressure that is as low as possible. However, since the $C_{3-}$ head product is to be obtained simultaneously under a maximally high pressure, e.g. at least 45 bar, especially at least 50 bar, the rectification must be conducted in at least two stages. The three-stage rectification according to this invention offers the further advantage, in this connection, that, by returning the head product of the second stage into the upper section of the first stage, the reflux for the first stage can at least in part be condensed at ambient temperature. If the head product of the third stage is returned—as indicated in the preferred embodiment—into the lower section of the second stage, the bottom product of the second stage can also be utilized directly as reflux for the third stage. This affords the advantage that the head product of the third stage contains a proportion—tolerable in this case—of $C_{3+}$ hydrocarbons, e.g., about 30 to 90 , especially 60 to 70 mol percent, lowering the boiling pressure of the head product of the third stage and thus permitting rectification under a lower pressure. The process of this invention provides, besides the lowering of the consumption of refrigerant, a more economical design for the apparatus. In this connection, the head product of the first rectifying column is obtained under a high pressure, suitable for a subsequent scrubbing operation. Thus, the present invention is particularly applicable to a process wherein higher hydrocarbons are separated by rectification as the bottoms product, and methane, ethane, and the major portion of propane constitute, together with hydrogen sulfide and carbon dioxide, the head product of the rectification, and wherein a physical scrubbing step is employed to obtain from the head product, a methane-containing gas substantially free of $H_2S$ and $CO_2$ as for exampled described in DOS No. 2,828,498.

In accordance with an especially advantageous embodiment of the process of this invention, the rectification in the second stage is performed under a pressure lower than in the first stage, and, in the third stage, under a pressure lower than in the second stage. In particular, the rectification in the first stage is performed under a pressure of 45–75 bar, in the second stage under a pressure of 30–45 bar, and in the third stage under a pressure of 10–30 bar. In general, it is preferred that the pressure difference between the first stage and second stage be about 5 to 40, especially 10 to 30 bar, and for the pressure difference between the second stage and third stage be about 5 to 30, especially about 10 to 25 bar. Ethane, propane, butane and similar hydrocarbons show a critical pressure of about 35–50 bar. To make a higher operation pressure feasible the concentration of $H_2S$ which has a critical pressure of move than 90 bar has to be increased so much that the critical pressure of the mixture exceeds the operating pressure by at least 3 bar. Lowering of the pressure in the second stage as compared with the pressure in the first stage provides for an improved $H_2S$-purity of the sump product since, owing to critical pressure considerations, a high column pressure is permissible only with a high $H_2S$ content in the sump. Thereby, in turn, recycling from the third stage can be reduced so that, overall, savings are obtained in the apparatus layout of the facility.

Of additional advantage is that at the lower pressures and associated temperatures of rectification, condensation of the head product can still be effected at ambient temperature. This condensation can thus be performed either against cooling water having a temperature of generally about 15° to 35° C. or against air having a temperature of generally about 25° to 45° C. This considerably reduces the need and associated costs for energy-consuming refrigerant produced by conventional external refrigeration cycles.

To be able to maintain the head temperature at ambient temperature in the second stage, it is necessary, though, to have only minor proportions of higher-boiling hydrocarbons in the liquid stream to be rectified therein. Thus, the concentration of $C_{2-}$ components must be so low that the boiling temperature of the head product of the second stage is only insignificantly affected. According to the invention, the provision is made, therefore, that an ethane concentration of 0.01–1.0 mol-%, preferably 0.1–0.6 mol-%, is maintained in the bottoms product of the first stage which is passed as feed to the second stage.

To further improve the separation efficiency of the process of this invention, it is provided according to a preferred embodiment of the invention, that the condensed head product of the third stage is introduced into the second stage at a point where the concentration of the components of the condensed head product is substantially the same concentration as the liquid in the column.

The present invention is especially applicable to the separation of gases of the following ranges of composition in mol-%.

| Component | General | Preferred |
| --- | --- | --- |
| $CH_4$ | 40–80 | 45–70 |
| $C_2$ | 0,5–20 | 1–10 |
| $C_3$ | 0,2–15 | 1–10 |
| $C_{4+}$ | 0,1–20 | 1–10 |
| $N_2$ | 0–5 | 0–3 |
| $CO_2$ | 5–50 | 7–30 |
| $H_2S$ | 5–50 | 7–30 |

The invention moreover concerns an apparatus for conducting the process, said apparatus comprising first a rectifying column means; second rectifying column means connected downstream of the first rectifying column means, the bottom of the first rectifying column means being connected by a conduit with the lower section of the second rectifying column means, a return conduit being provided between the head of the second rectifying column means and the upper section of the first rectifying column means; a third rectifying column means connected downstream of the second rectifying column means, the upper section of this third rectifying column means being connected by a conduit with the bottom of the second rectifying column means and optionally being provided with a return conduit from the head to the lower section of the second column means. In this connection, condenser means are provided in the return conduits for condensation of the head product at ambient temperature.

BRIEF DESCRIPTION OF DRAWING

The attached drawing is a schematic illustration or a preferred embodiment of the invention.

DETAILED DESCRIPTION

Via conduit 1, 16,200 kmol/h of a gas is fed into the plant having a temperature of 303 K, a pressure of 70 bar, and the following composition:

| | |
| --- | --- |
| $CH_4$ | 49.98 mol % |
| $C_2H_6$ | 1.61 mol % |
| $C_3H_8$ | 0.97 mol % |
| $C_{4+}$ HC | 6.12 mol % |
| $N_2$ | 2.45 mol % |
| $CO_2$ | 14.22 mol % |
| $H_2S$ | 24.65 mol % |

The gas is expanded to the operating pressure of the first rectifying column (valve 2) and charged into the rectifying column 3 at the center thereof. The rectifying column is equipped with an externally cooled head condenser, a reboiler, and 30 theoretical plates. The temperature of the top overhead gas is 277 K, and the reboiler temperature is 404 K.

The column operates under a pressure of 60 bar. The critical pressure of the rectified liquid is above 70 bar at any location of the column thereby providing a sufficient safety margin with respect to the operating pressure. By way of conduit 4, 15,215 kmol/h of a gas having the following composition is discharged from the phase separator 31 at the head of the rectifying column 3:

| | |
| --- | --- |
| $CH_4$ | 53.21 mol % |
| $C_2H_6$ | 1.72 mol % |
| $C_3H_8$ | 1.02 mol % |
| $C_{4+}$ HC | 0.06 mol % |
| $N_2$ | 2.61 mol % |
| $CO_2$ | 15.14 mol % |
| $H_2S$ | 26.24 mol % |

About 3,500 kmol/h of liquid from phase separator 31 is recycled to rectifying column 3.

By way of conduit 5, there is withdrawn from rectifying column 3 2,515 kmol/h of a bottoms mixture having the following composition:

| | |
| --- | --- |
| $CH_4$ | 0 mol % |
| $C_2H_6$ | 0.4 mol % |
| $C_3H_8$ | 2.68 mol % |
| $C_{4+}$ HC | 31.16 mol % |
| $N_2$ | 0 mol % |
| $CO_2$ | 0.03 mol % |
| $H_2S$ | 57.73 mol % |

The bottoms mixture (2,515 kmol/h), after pressure reduction, is introduced into the lower section of a second rectifying column 6 having 20 theoretical plates, a water cooled head condenser and a reboiler. The temperature of the top overhead is 320 K, the reboiler temperature is 473 K, and column operating pressure is 35 bar. From the phase separator 61 at the head of column 6, 1,531 kmol/h of a liquid mixture, condensed against cooling water, is withdrawn and recycled via conduit 7 to the head of the first rectifying column 3. The remaining liquid in phase separator 61 functions as reflux for column 6 and amounts to about 3.000 kmol/h. In these steps, the liquid mixture in phase separator 61 has the following composition:

| | |
| --- | --- |
| $CH_4$ | 0 mol % |
| $C_2H_6$ | 0.66 mol % |
| $C_3H_8$ | 4.25 mol % |
| $C_{4+}$ HC | 0.20 mol % |
| $N_2$ | 0 mol % |
| $CO_2$ | 0.04 mol % |

| | |
|---|---|
| -continued | |
| H$_2$S | 94.85 mol % |

The top overhead is supposed to be completely condensable against cooling water or air. If there remains, however, a small amount of incondensable gases in separator 61 due to irregular operation it can be withdrawn and led to a suitable process line or to fuel.

By way of conduit 8, there is withdrawn 1,798 kmol/h of a bottoms mixture from the second rectifying column 6 having the following composition:

| | |
|---|---|
| CH$_4$ | 0 mol % |
| C$_2$H$_6$ | 0.05 mol % |
| C$_3$H$_8$ | 1.82 mol % |
| C$_{4+}$ HC | 83.13 mol % |
| N$_2$, CO$_2$ | 0 mol % |
| H$_2$S | 15.00 mol % |

This mixture after pressure reduction is introduced into the third rectifying column 9 at the head thereof, the liquid phase of the mixture functioning as reflux. The gaseous head product from column 9 is liquefied at 320 K by means of a partial condenser, for example against cooling water. The bottoms temperature is 530 K. The column operates under a pressure of 15 bar and has about 20 theoretical plates.

From the top of column 9, 814 kmol/h of an overhead gas is withdrawn having the following composition:

| | |
|---|---|
| CH$_4$ | 0 mol % |
| C$_2$H$_6$ | 0.11 mol % |
| C$_3$H$_8$ | 3.71 mol % |
| C$_{4+}$ HC | 63.04 mol % |
| N$_2$, CO$_2$ | 0 mol % |
| H$_2$S | 33.14 mol % |

This mixture is condensed and passed into phase separator 91. The resultant condensate (814 kmol/h) is recycled via conduit 10 into the lower section of rectifying column 6, namely at a point in the column wherein the column liquid has substantially the same concentration of components, i.e. especially above the feed point of conduit 5. The gas withdrawal of separator 91 has the same function of that one assigned to separator 61.

A liquid phase having the composition set forth below is obtained in an amount of 984.6 kmol/h at the bottom of column 9:

| | |
|---|---|
| CH$_4$, C$_2$H$_6$ | 0 mol % |
| C$_3$H$_8$ | 0.25 mol % |
| C$_{4+}$ HC | 99.75 mol % |
| N$_2$, CO$_2$, H$_2$S | 0 mol % |

The C$_{4+}$ hydrocarbon condensate obtained by the process of this invention is thus free of sour gases and contains only a minor amount of C$_3$ hydrocarbons. It is discharged via conduit 11 and can be processed further by conventional means. Separated butane gas, for example, has many uses.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

We claim:

1. A process for the fractionation of a gaseous mixture under pressure, said mixture containing methane, C$_2$, C$_3$, C$_{4+}$ inert gas, and sour gases comprising hydrogen sulfide, and carbon dioxide, the total of the sour gases being at least 1 mol %, wherein the higher hydrocarbons are separated by rectification as the bottoms product, the improvement comprising conducting the rectification in three rectification stages: in the first rectification stage, separating a head product substantially free of C$_{4+}$ hydrocarbons; feeding the bottoms of the first rectification stage to the second rectification stage, and separating therein further C$_{3-}$ hydrocarbons and a fraction of the hydrogen sulfide as the head product and recycling the second stage head product into the first rectification stage to function therein at least in part as reflux; passing bottoms product of the second rectification stage into the third rectification stage, and separating residual hydrogen sulfide and residual proportions of C$_{3-}$ hydrocarbons as the head product; and withdrawing H$_2$S-free C$_{4+}$ hydrocarbons bottoms product from the third rectification stage.

2. A process according to claim 1, wherein the overhead from the first stage is scrubbed with a physical solvent to remove sour gases.

3. A process according to claim 1, wherein third stage head product is recycled to the second stage.

4. A process according to claim 1, wherein the rectification, in the second stage, is conducted under a lower pressure than in the first stage and, in the third stage, under a lower pressure than in the second stage.

5. A process according to claim 4, characterized in that the rectification is conducted, in the first stage, under a pressure of 45-75 bar; in the second stage, under a pressure of 30-45 bar; and in the third stage, under a pressure of 10-30 bar.

6. A process according to claim 1, wherein the head product of the second stage is condensed at ambient temperature before being returned into the preceding stage.

7. A process according to claim 3, wherein the head product of the third stage is condensed at ambient temperature before being returned into the second stage.

8. A process according to claim 7, wherein the head product of the second stage is condensed at ambient temprature before being returned into the preceding stage.

9. A process according to claim 1, wherein the bottoms product of the first stage has an ethane concentration of 0.01-1.0 mol-%.

10. A process according to claim 1, wherein the bottoms product of the first stage has an ethane concentration of preferably 0.1-0.6 mol-%.

11. A process according to claim 3, wherein the head product of the third stage is introduced into the second stage at a point at where the concentration of the components in the third stage head product is substantially the same as the concentration of the components in the second stage column liquid.

12. A process according to claim 5, wherein the bottoms product of the first stage has an ethane concentration of 0.01-1.0 mol-%.

13. A process according to claim 12, wherein the head product of the second stage is condensed at ambient temperature before being returned into the preceding stage.

14. A process according to claim 6, wherein the bottoms product of the first stage has an ethane concentration of 0.01–1.0 mol-%.

15. A process for the fractionation of a gaseous mixture under pressure, said mixture containing methane, $C_2$, $C_3$, $C_{4+}$ inert gas, and sour gases comprising hydrogen sulfide, and carbon dioxide, the total of the sour gases being at least 1 mole %, wherein the higher hydrocarbons are separated by rectification as the bottoms product, the improvement comprising conducting the rectification in three rectification stages: in the first rectification stage, separating a head product substantially free of $C_{4+}$ hydrocarbons; feeding the bottoms of the first rectification stage to the second rectification stage, and separating therein further $C_{3-}$ hydrocarbons and a fraction of the hydrogen sulfide as the head product and recycling the second rectification stage head product into the first rectification stage; passing botoms product of the second rectification stage into the third rectification stage, and separating residual hydrogen sulfide and residual proportions of $C_{3-}$ hydrocarbons as the head product; and withdrawing $H_2S$-free $C_{4+}$ hydrocarbons bottoms product from the third rectification stage.

16. A process according to claim 1, the total of the sour gases being at least 5 mol %.

17. A process according to claim 1, wherein said gaseous mixture has the following composition in mole %: 40–80 $CH_4$, 0.5–20 $C_2$, 0.2–15 $C_3$, 0.1–20 $C_{4+}$, 0–5 $N_2$, 5–50 $CO_2$, and 5–50 $H_2S$.

18. A process according to claim 1, wherein the gaseous mixture has a composition in mole % of: 45–70 $CH_4$, 1–10 $C_2$, 1–10 $C_3$, 1–10 $C_{4+}$, 0–3 $N_2$, 7–30 $CO_2$, and 7–30 $H_2S$.

19. A process according to claim 1, conducted in the absence of a step of absorbing the gaseous mixture with a hydrocarbon oil absorbent.

* * * * *